US006482170B1

(12) United States Patent
Andersen

(10) Patent No.: US 6,482,170 B1
(45) Date of Patent: Nov. 19, 2002

(54) APPARATUS AND METHOD FOR RELIEVING GASTRIC PRESSURE DURING ENTERAL FEEDING

(75) Inventor: Erik Andersen, Gurnee, IL (US)

(73) Assignee: Corpak, Inc., Wheeling, IL (US)

(*) Notice: Subject to any disclaimer, the term of this patent is extended or adjusted under 35 U.S.C. 154(b) by 113 days.

(21) Appl. No.: 09/665,194

(22) Filed: Sep. 18, 2000

(51) Int. Cl.[7] .......... A61M 1/00

(52) U.S. Cl. .......... 604/27; 604/19; 604/48

(58) Field of Search .......... 604/19, 27, 48, 604/93.01, 100.01, 99.01

(56) References Cited

U.S. PATENT DOCUMENTS 4,464,175 A * 8/1984 Altman et al. .......... 604/99.01
4,690,138 A * 9/1987 Heyden .......... 604/100.01 X

OTHER PUBLICATIONS

The FARRELL VALVE Enteral Gastric Pressure Relief System advertisement (1999).

* cited by examiner

*Primary Examiner*—Chen-Wen Jiang
(74) *Attorney, Agent, or Firm*—Bell, Boyd & Lloyd LLC

(57) ABSTRACT

A gastric pressure relief apparatus for incorporation within an enteral feeding system, including an enteral feeding container, an administrative tube and an enteral feeding tube. The apparatus comprises a gas and liquid-receiving reservoir with a gas vent to ambient atmosphere, a length of tube secured to the reservoir at one end and joined to the enteral feeding tube at another end and connector means for joining the administrative tube to the length of tube to be oriented at a point below that of an enterally-fed patient's stomach. The length of tube includes volumetric indicia to allow for measurement of refluxed fluid and subsequent adjustment of fluid administration.

19 Claims, 1 Drawing Sheet

APPARATUS AND METHOD FOR RELIEVING GASTRIC PRESSURE DURING ENTERAL FEEDING

TECHNICAL FIELD

The present invention generally relates to enteral nutrition wherein fluid nutrients are administered to the human gastrointestinal tract through an enteral feeding tube and, in particular, to improvements to a device for relieving gastric pressure in neonatal and pediatric patients during enteral feeding.

BACKGROUND OF THE INVENTION

Enteral nutrition is a form of hyperalimentation and metabolic support in which nutrient formulas or medicaments are delivered directly to the gastrointestinal tract, either the stomach or the duodenum. Nutrient administration is accomplished through use of an enteral feeding system generally comprising an enteral feeding container, usually a distensible bag suspended above patient level, joined to a length of flexible administration tubing. The proximal end of the administration tubing, which is joined to an outlet port in the enteral feeding bag, may include a drip chamber-tube clamp arrangement for determining flow rate. The distal end of the administration tubing carries a male luer adaptor for coupling with a female luer adaptor disposed on a distal end of an enteral feeding tube. U.S. Pat. No. 4,490,143 generally discloses the arrangement of elements utilized in an enteral feeding system. Intubation of the enteral feeding tube may be through naso-pharyngeal passage or through oral intubation. The flow rate of fluid nutrient through the enteral feeding tube is achieved through either gravity feed or use of an enteral feeding pump disposed at a generally intermediate position along the administration tubing.

During enteral feeding excessive gastric pressure may result through accumulation of gas or liquid resulting from stomach contractions, movement of the patient's abdomen, crying or through normal formation of gas. Typically the body relieves such excess gastric pressure through expulsion of accumulated gas or liquid through a burping response. However, in a patient undergoing enteral feeding in which fluid nutrients are being continually fed to the gastrointestinal tract, upward expulsion of gastric reflux materials is highly undesirable. More importantly, reflux of gas or liquid through the enteral feeding tube cannot occur. Though gastric reflux pressure created by even limited episodes of stomach movement or crying may exceed several feet of water, such reflux pressure is inadequate to overcome the greater forward fluid pressure present within the enteral feeding tube. This greater fluid pressure is developed because the height of the column of fluid nutrient in the enteral feeding system stands well above the level of the patient's stomach. Fluid pressure is further increased through the use of the enteral feeding pump. In addition, tube set clamps along the administration tubing also prevent reflux of excessive gastric gas or liquid through the enteral feeding tube.

Because gastric reflux pressure cannot overcome the greater forward fluid pressure within the enteral feeding tube, reflux materials are expelled upward from the stomach through the esophagus and are expressed out of the mouth, where the enteral feeding tube is orally intubated, or through the nasal passages, where naso-pharyngeal intubation has been utilized. In the latter, it is possible for the patient to inhale the reflux materials into the lungs with possible risk of aspiration pneumonia. The problem of relief of gastric reflux pressure is most accute in neonates, infants and small children in which gastric pressure may rapidly accumulate through periodic episodes of crying and because such patients have yet to develop control over the burping response as a means of gastric pressure relief. However, it is not unusual for adult patients undergoing enteral feeding to experience occasional difficulties with gastric reflux pressure relief.

Gastric pressure relief devices such as device 10 in FIG. 1 have been developed to permit relief of gastric reflux pressure through the enteral feeding tube to avoid uncontrolled upward expulsion of reflux materials through the burping response. Device 10 also prevents introduction of air into any portion of the enteral feeding system, particularly the enteral feeding tube. Further, because the fluid refluxed by a patient generally comprises the nutrient formula being administered to the patient, after device 10 relieves gastric reflux pressure, the refluxed fluid nutrient is returned to the enteral feeding tube for delivery to the patient. However, the quantity of refluxed fluid nutrient, particularly fluid which collects within tube line 18 is often unknown. This adversely impacts accurate enteral administration of fluid nutrient, particularly since a selected quantity of nutrient is administered over a given period of time. Hence, prior to the development of the improvements to device 10 as disclosed herein, a need existed for a gastric reflux pressure relief device which temporarily collects, accurately measures and returns refluxed nutrient formula to the enteral feeding tube.

SUMMARY OF THE INVENTION

According to the present invention improvements to a gastric reflux pressure relief device have been developed for in-line incorporation into an enteral feeding system. The pressure relief device is interposed between the distal end of an administration tubing and proximal end of the enteral feeding tube for capturing refluxed fluid.

The pressure relief device includes a selected length of pressure relief tubing having a fluid collection reservoir on a proximal end. A male luer adaptor is disposed at a distal end of the relief tubing for coupling with a female luer adaptor at a proximal end of an enteral feeding tube. Joined along a selected position on the relief tubing is a Y-connector for receiving the male luer adaptor commonly utilized on the distal end of enteral administration tubing. Hence, the relief tubing is in fluid communication with both a source of fluid nutrient and the enteral feeding tube. The Y-connector is interposed at a position about ⅔ of the length of the relief tubing so that the segment of tubing proximal to the Y-connector defines a pressure relief segment while the segment of the tubing distal to the Y-connector delivers fluid nutrient received from the administration tubing to the enteral feeding tubing. The reflux material collection reservoir, preferably a flexible plastic tail-feeding bag, is vented to the ambient atmosphere. Where reflux materials include gas, the gas is released from the present pressure relief apparatus through the vent. On the other hand, where the reflux materials include fluid, then the reservoir temporarily collects and retains the fluid before gradual return and delivery to the patient. Though the collection reservoir is vented to the ambient atmosphere, so long as the Y-connector is positioned at or below the patient's stomach level, a standing column of fluid nutrient will be maintained above the Y-connector, thereby preventing suction of air into the enteral feeding system through the reservoir gas vent.

It has been found that because the reservoir has inner dimensions larger than the relief tubing, the reservoir best functions to receive and expel refluxed gas. Though the reservoir has volumetric markings, refluxed formula rarely enters the reservoir. Instead, formula most commonly is refluxed into the relief tubing above the Y-connector. As a result, the relief tubing may carry a meaningful quantity of formula, particularly, for neonatal patients. Hence, the relief device has been improved by providing the relief tubing with volumetric indicia or markings.

The present invention will be more fully described in the following detailed description with reference being made to the drawings and the Claims appended thereto.

DETAILED DESCRIPTION

Figure 2:
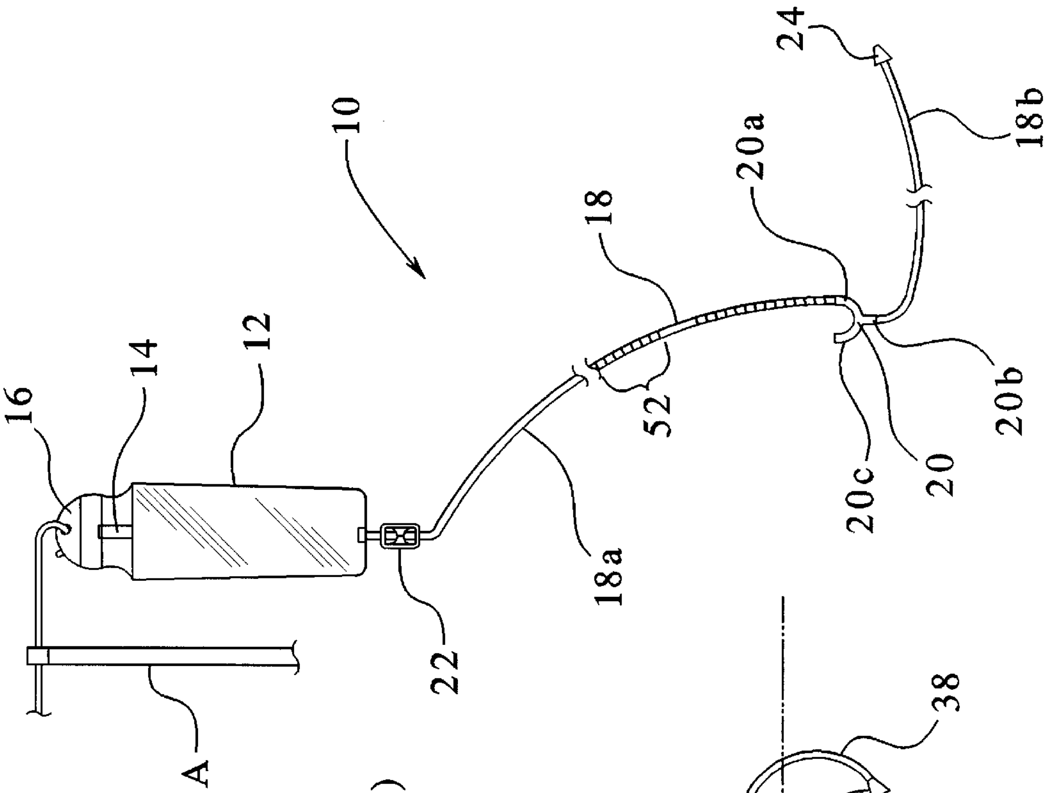

The term “fluid” as used herein shall refer to and include both gas and liquid physical states. Referring now to the drawings, FIGS. 1 and 2 disclose a gastric pressure relief device known in the art generally referenced by 10. As will later be explained in greater detail, relief apparatus 10 is interposed between a distal end of enteral feeding administration tubing and a proximal end of an enteral feeding tube. Relief apparatus 10 generally comprises at a proximal end a reflux material collection reservoir 12, preferably a distensible bag to receive gas or fluid materials refluxed during gastric pressure relief. Reservoir 12 is vented to the ambient atmosphere through gas vent 14 and is suspended from a support standard by a hanger tab 16. Reservoir 12 is joined to a length of tubing 18 placing reservoir 12 in fluid communication with both the enteral feeding tube and the administration tubing. Disposed preferably at about ⅔ the length of tubing 18 is a connector 20 for joining tube 18 with a distal portion of the administration tubing. Preferably, connector 20 is a Y-shape connector which separates tubing 18 into two segments, although any shaped connector known or used in the art is suitable so long as the fluid continuity of tube 18 can be maintained. For example, a small sleeve molded into an opening cut in the side wall of tubing 18 to receive a distal portion of administration tubing without severing tubing 18 into segments may also be suitable.

As best disclosed in FIG. 2, connector 20 apportions tubing 18 to define a pressure relief segment **18*a* proximal to connector 20 and seated within area 20*a* of connector and a fluid delivery segment 18*b* distal to connector 20 and seated within arm 20*b* of connector 20. Preferably carried on relief segment 18*a* is a slideable tube set clamp 22 utilized to close relief segment 18*a* causing pressure relief apparatus 10** to become inoperative.

A proximal end of fluid delivery segment **18*b* is joined to arm 20*b* of connector 20. A distal end of fluid delivery segment 18*b* carries a male luer adaptor 24 to be inserted into a female luer adaptor carried on a proximal end of the enteral feeding tube, which will be discussed later in greater detail. Fluid delivery segment 18*b* serves to receive fluid nutrient from administration tubing and deliver such fluid to the enteral feeding tube. In addition, in conditions of excessive gastric pressure, fluid delivery segment 18*b* passes reflux materials, gas or liquid, through connector 20 into pressure relief segment 18*a*, and, if necessary, into collection reservoir 12 as well. Any reflux gas which passes through fluid delivery segment 18*b* which is channeled into relief segment 18*a* continues to pass upward through collection reservoir 12, through gas vent 14** and into the ambient atmosphere.

Reservoir 12 is a distensible bag preferably made from a flexible elastomeric plastic such as polyethylene or polyvinylchloride. However, it is conceivable that reservoir 12 could also embody a more shape-retentive container such as a polyethylene plastic bottle. Reservoir 12 must have adequate capacity to receive a substantial amount of reflux material in the event of repeated episodes of excessive gastric pressure. For example, when relief apparatus 10 is utilized in enteral feeding of infants, reservoir 12 should have a fluid capacity of approximately 500 ml.

Figure 1:
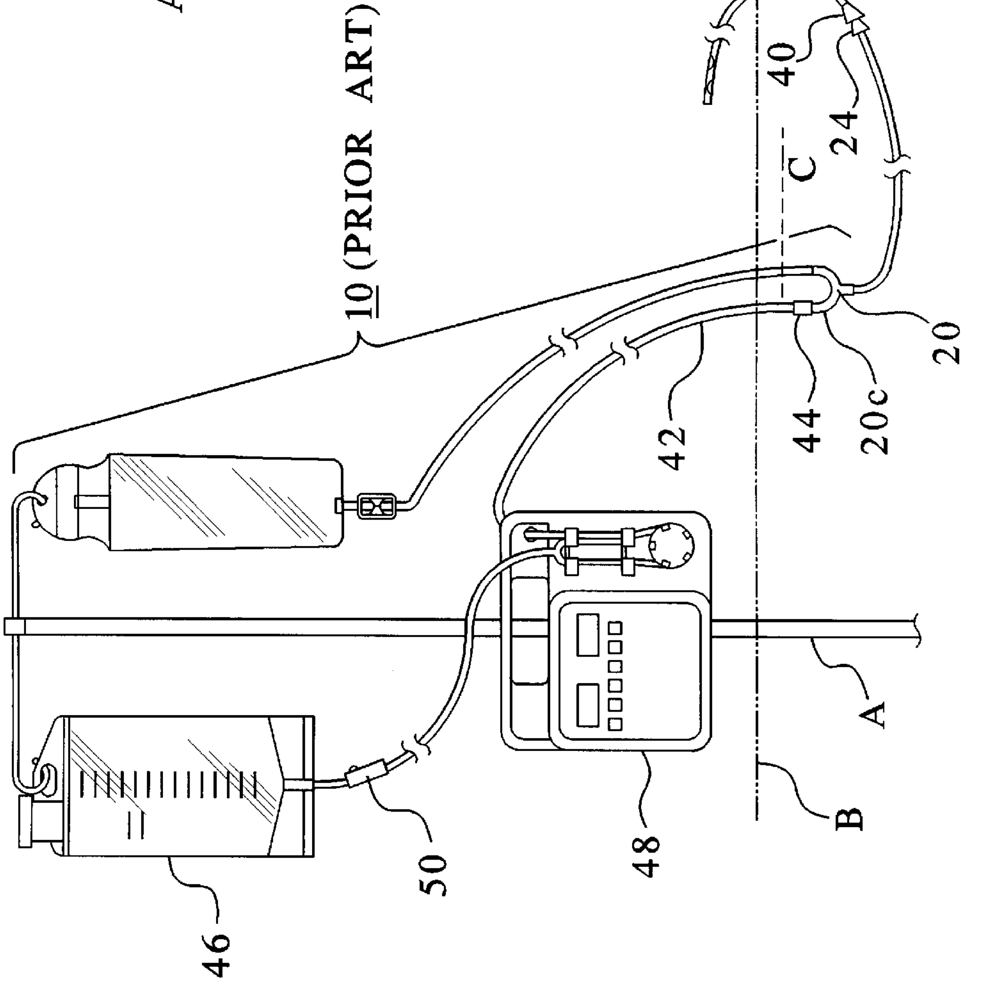
FIG. 1 is a perspective view of a gastric pressure relief device known in the art set off by bracket, incorporated within an enteral feeding system; and, FIG. 2 is a fragmented perspective view of the known pressure relief device with the improvements thereto.

The use and operation of relief apparatus 10 is disclosed in FIG. 1. As previously discussed, the distal portion of relief apparatus 10 is joined to an enteral feeding tube 38 of a selected length and diameter suited for the particular patient. Specifically, male luer adaptor 24 disposed on the distal end of fluid delivery segment **18*b* seats within a female luer adaptor 40 disposed on a proximal end of enteral feeding tube 38. Next, a distal end of an administration tubing 42 is joined to relief apparatus 10 through connection with open arm 20*a* of connector 20. Specifically, a male luer adaptor 44 disposed on the distal end of administration tubing 42 seats within open arm 20*c* of connector 20. Finally, reservoir 12 is suspended by hanger 16 from an available arm of a common intravenous suspension standard A. Clamp 22 disposed on pressure relief segment 18*a* would be in a closed position so as to maintain relief apparatus 10** in an inoperative mode.

An enteral feeding container 46 containing a selected nutrient formula is also suspended from support standard A preferably at the same height and level as reservoir 12. The flow rate for delivery of nutrient formula from enteral feeding container 46 through administration tubing 42 may be accomplished through use of an enteral feeding pump 48 in combination with use of a tube set clamp 50, preferably a roller-type clamp as disclosed in FIG. 1. Fluid flow rate may also be achieved through gravity feed controlled through the combination of a drip chamber and a tubing clamp (not shown).

Enteral feeding begins after priming of administration tubing 42. In order to insure that there are no occlusions within feeding tube 38, a small amount of nutrient formula is initially administered to the patient. After any occlusions have been overcome, clamp 22 of relief apparatus 10 is opened, thereby activating pressure relief apparatus 10.

Relief apparatus 10 is essentially an open system, i.e., reservoir 12 is vented to ambient atmospheric pressure. Hence, to avoid introduction of air into enteral feeding tube 38 through tubing 18, pressure relief apparatus 10 must be oriented in such a manner so as to assure the presence of a small column of nutrient formula within pressure relief segment **18*a*. This is accomplished by positioning connector 20, and as a result the distal end of relief segment 18*a* at or slightly below the level of the patient’s stomach. For reference purposes, patient level is indicated in FIG. 1 by broken line B. So long as connector 20 maintains the distal end of pressure relief segment 18*a* at or below patient level, then a small column of nutrient formula is developed and remains suspended within a distal portion of relief segment 18*a* with the miniscus of the column generally at a position marked by broken line C in FIG. 1. This column of fluid prevents air from being drawn into fluid delivery segment 18*b* and, ultimately, into enteral feeding tube 38**.

Another unique aspect of maintaining the fluid column is that the height of such column has been observed to fluctuate in response to greater or lesser gastric pressure (ambient atmospheric pressure being a relative constant). When the height of the fluid column has increased within relief segment 18*a*, the cause may be increased gastric pressure or partial occlusion of enteral feeding tube 38.

In the course of normal operation of apparatus 10, the height of the column of fluid within relief segment 18*a* may rise and enter collection reservoir 12 in two situations. First, fluid will rise and enter reservoir 12 if enteral feeding tube 38 becomes occluded during feeding. Secondly, if the patient accumulates excessive gastric pressure, fluid or gas will reflux from the patient's stomach through enteral feeding tube 38 to fluid delivery segment 18*b*, then to segment 18*a* for collection in reservoir 12. Any gas within the reflux materials will separate and escape through vent 14.

Because the relief tubing 18*a* may carry a meaningful quantity of formula, particularly, for neonatal patients, the relief device 10 has been improved by providing the relief tubing 18*a* with volumetric markings 52. This allows the monitoring of refluxed formula to ensure that the patient is receiving the prescribed amount.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof Therefore, it is intended that the invention not be limited to a particular embodiment disclosed as the best mode contemplated for carrying out the invention, but that the invention will include all embodiments falling within the scope of the appended claims.

I claim:

1. In an apparatus for relieving gastric pressure during enteral feeding of neonatal and pediatric patients, the apparatus being interposed between a fluid nutrient source and an enteral feeding tube, the apparatus having gastric relief tubing for collecting reflux fluids from the patients stomach, a proximal end of the tubing being in fluid communication with ambient atmosphere, a distal end of the tubing being coupled to a proximal end of the enteral feeding tube, the apparatus further including connector means for fluid communicatively coupling the fluid nutrient source with the tubing, the connector means being interposed along the length of the tubing, the improvement comprising:

the gastric relief tubing having volumetric markings selected to measure quantities of fluid periodically refluxed during enteral feeding of neonatal and pediatric patients.

2. The apparatus of claim 1 wherein the volumetric markings are in increments of one milliliter.

3. A gastric pressure relief device for use in neonatal and pediatric enteral feeding systems, the device interposed between a source of enteral nutrient and an enteral feeding tube for enteral nutrient delivery into a patient, the device comprising:

a gastric relief tube having a proximal end, a distal end, and having volumetric indicia thereon, the distal end in fluid communication with a proximal end of the enteral feeding tube, the gastric relief tube further in fluid communication with ambient atmosphere;

a reservoir in fluid communication with the proximal end of the gastric relief tube, the reservoir vented to ambient atmosphere and adapted to collect reflux fluids from the patient's stomach; and a connector adapted to connect the source of enteral nutrient with the gastric relief tubing and selectively positionable with respect to the gastric relief tubing, such that when the connector is oriented below the patient's stomach and the reservoir is oriented above the patient's stomach, excess gastric pressure is relieved from the patient by reflux of fluid through the enteral feeding tube and into the gastric relief tube for collection within the reservoir; the volumetric indicia of the gastric relief tube allowing measurement of the refluxed fluid within the gastric relief tube.

4. The device of claim 3, wherein the volumetric markings are in increments of one milliliter.

5. The device of claim 3, wherein the connector is a generally Y-shaped tubular connector.

6. A method for enterally feeding neonatal and pediatric patients a selected volume of fluid nutrient for a selected duration comprising the steps of:

interposing between a fluid nutrient source and an enteral feeding tube an apparatus having a selected length of gastric relief tubing for collecting reflux fluids, a proximal end of the tubing being in fluid communication with ambient atmosphere, a distal end of the tubing being coupled to a proximal end of the enteral feeding tube, the tubing having volumetric markings along the preselected length; and assessing periodically the quantity of fluid refluxed during enteral feeding.

7. The method of claim 6, further comprising the step of adjusting the duration of enteral feeding.

8. The method of claim 6, further comprising the step of adjusting the volume of fluid nutrient.

9. A method for enterally administering a selected volume of fluid nutrient to neonatal and pediatric patients for a selected duration, the method comprising the steps of:

interposing between a fluid nutrient source and an enteral feeding tube an apparatus having a selected length of gastric relief tubing for collecting reflux fluids, said gastric relief tubing having volumetric markings along said preselected length, a proximal end of the tubing being in fluid communication with ambient atmosphere, a distal end of the tubing being coupled to a proximal end of the enteral feeding tube; and measuring the volume of fluid refluxed into the gastric relief tubing during enteral feeding via the volumetric markings.

10. A gastric pressure relief device for use in conjunction with at least one feeding fluid container and a feeding tube received by a patient, the gastric pressure relief device comprising:

a relief tube in fluid communication with the feeding fluid container and the feeding tube, the relief tube capable of holding a known volume of fluid along a selected length, a plurality of measurement markings along the selected length of the relief tube; and a reservoir in fluid communication with the relief tube, the reservoir vented to atmosphere.

11. The gastric pressure relief device of claim 10, which includes a connector connected to the relief tube, said connector bringing the relief tube in fluid communication with the feeding fluid container.

12. The gastric pressure relief device of claim 11, wherein the feeding fluid container has a position above the patient's stomach.

13. The gastric pressure relief device of claim 11, wherein the reservoir has a position above the patient's stomach.

14. The gastric pressure relief device of claim 11, wherein the patient comprises a child.

15. An enteral feeding system for use in conjunction with a feeding tube received by a patient, the enteral feeding system comprising:

at least one feeding fluid container supported by at least one support member; and a gastric pressure relief device in fluid communication with said feeding fluid container, said gastric pressure relief device including a relief tube having a first end and a second end, the first end in fluid communication with a reservoir, said reservoir vented to atmosphere, the second end of the relief tube adapted to be connected to the feeding tube, the relief tube capable of holding a known volume of fluid along a selected length, a plurality of measurement markings along the selected length of the relief tube.

16. The enteral feeding system of claim 16, wherein the gastric pressure relief device includes a connector connected to the relief tube, said connector bringing the relief tube in fluid communication with the feeding fluid container.

17. The enteral feeding system of claim 16, wherein the feeding fluid container has a position above the patient's stomach.

18. The enteral feeding system of claim 15, wherein the reservoir has a position above the patient's stomach.

19. The enteral feeding system of claim 15, wherein the patient comprises a child.

* * * * *